United States Patent
Hanna al-kass

(10) Patent No.: US 12,390,622 B2
(45) Date of Patent: Aug. 19, 2025

(54) FENESTRATED INFUSION BALLOON CATHETER AND METHODS OF USE

(71) Applicant: Farajallah Mounir Hanna al-kass, Glendale, CA (US)

(72) Inventor: Farajallah Mounir Hanna al-kass, Glendale, CA (US)

( * ) Notice: Subject to any disclaimer, the term of this patent is extended or adjusted under 35 U.S.C. 154(b) by 808 days.

(21) Appl. No.: 17/679,063

(22) Filed: Feb. 23, 2022

(65) Prior Publication Data

US 2022/0379098 A1 Dec. 1, 2022

Related U.S. Application Data

(60) Provisional application No. 63/155,187, filed on Mar. 1, 2021.

(51) Int. Cl.
*A61M 25/10* (2013.01)
*A61M 25/00* (2006.01)
*A61B 17/12* (2006.01)
*A61M 5/00* (2006.01)

(52) U.S. Cl.
CPC ........ *A61M 25/10* (2013.01); *A61M 25/0026* (2013.01); *A61B 17/12186* (2013.01); *A61M 5/007* (2013.01); *A61M 2025/105* (2013.01)

(58) Field of Classification Search
CPC .............. A61M 25/10; A61M 25/1018; A61M 25/1025; A61M 25/0026; A61M 25/0071; A61M 2025/1043; A61M 2025/105; A61M 2025/1061; A61M 2025/1072; A61M 2025/0057; A61M 5/007; A61M 5/1407; A61M 31/005; A61M 25/10181; A61M 25/1027; A61M 2025/1052; A61M 2025/1056; A61M 2025/107; A61M 2025/1077; A61M 2025/1086; A61B 17/12186
See application file for complete search history.

(56) References Cited

U.S. PATENT DOCUMENTS

| | | | | |
|---|---|---|---|---|
| 5,213,576 A | * | 5/1993 | Abiuso | A61M 16/0456 604/101.02 |
| 5,800,392 A | * | 9/1998 | Racchini | A61N 1/306 604/20 |
| 2010/0331817 A1 | * | 12/2010 | Schaeffer | A61M 25/1011 604/101.02 |
| 2014/0039358 A1 | * | 2/2014 | Zhou | A61M 37/0092 601/3 |

* cited by examiner

*Primary Examiner* — Kevin C Sirmons
*Assistant Examiner* — Alexandra Lalonde
(74) *Attorney, Agent, or Firm* — Boris Leschinsky

(57) ABSTRACT

A dual-lumen injection catheter is equipped with a distal balloon featuring one or more fenestration or openings on the distal portion of the distal balloon. This allows injection of a contrast agent in parallel to an injection of an embolic agent and better control over a delivery of a therapeutic agent for cancer treatments, bleeding or other purposes.

3 Claims, 2 Drawing Sheets

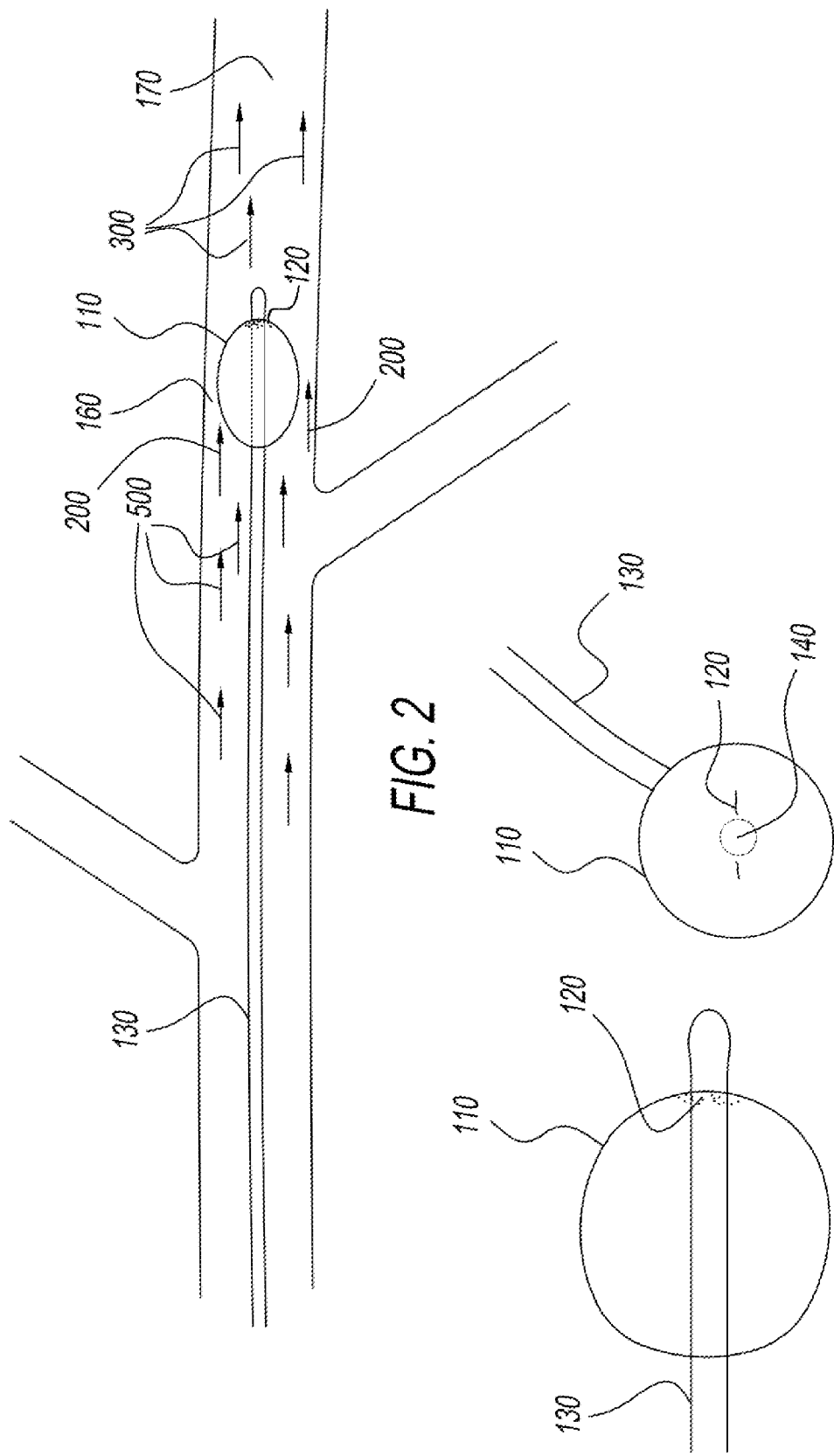

FENESTRATED INFUSION BALLOON CATHETER AND METHODS OF USE

CROSS-REFERENCE DATA

The present patent application claims a priority date benefit from co-pending U.S. Provisional Patent Application No. 63/155,187 filed 1 Mar. 2021 by the same inventor and entitled "Fenestrated Infusion Balloon Catheter", which is incorporated herein by reference in its entirety.

BACKGROUND

Without limiting the scope of the invention, its background is described in connection with catheters configured for injection of liquid or particle-containing embolic agents. More particularly, the invention describes a novel infusion catheter and methods of using thereof during embolization procedures. The catheter features an inflatable balloon at the distal end thereof, wherein the balloon is equipped with one or more openings configured for infusion of the desired liquid into the blood vessel during its use.

Certain cancers may be treated by tumor embolization. In broad terms, tumor embolization is a minimally invasive procedure in which a small, thin tube (referred hereto as a catheter) is guided into the feeding arteries of a tumor in order either to shut down the blood supply to the tumor or deliver tumor-killing therapy directly to the tumor.

Several different therapies are offered to cancer patients and can be customized depending on the type and location of the tumors. For instance, uterine fibroids (benign tumors) respond well to embolization with small particles that block off the blood flow to the fibroids. Certain liver tumors respond best to embolization with small beads infused with chemotherapy. Other liver tumors respond well to embolization with radioactive particles that kill tumors with radiation.

Embolization has several benefits, such as:
Relieving symptoms, such as heavy bleeding in women who have uterine fibroids
Shrinking tumors to allow surgical removal or bridging to transplant surgery.
Reducing blood loss during surgery to remove a tumor
Slowing tumor growth (as a palliative treatment) when surgery or chemotherapy are not possible Imaging is important during a typical embolization procedure as it is critical to guide the catheter to the right vessel and observe proper delivery of the embolization or medication agent to the tumor. Injection of radiopaque dye is used during these procedures in combination with certain X-Ray and fluoroscopy techniques in order to access the progression and safety of the embolization process (visualize the vessel tree around the tumor, locate the catheter within the vessel tree, and making sure the embolic agents are flowing to the intended target.

Conventional infusion catheters have a varying degree of reflux that leads to nontargeted embolization. This happens when the flow of blood propagating downstream from the balloon tip towards the tumor is not sufficient to carry the entirety of the injected embolic material downstream. This situation is depicted in FIG. 1 showing a catheter 130 with a distal tip 140 located in the target vessel segment 170 with the surrounding blood flow 500 passing in the direction of the tumor located downstream from the catheter tip 140. When the balloon 110 is deflated or when the injection catheter is not equipped with an inflatable balloon at the distal end thereof, the pressure in the vessel segment 160 proximal to the location of the balloon is equal to the pressure in the distal vessel segment 170 and no pressure gradient exists across the balloon. An injection of the embolic material from the tip 140 of the injection catheter may cause (due to turbulence) some portion of the embolic material mixed with surrounding blood 400 to divert backward from the distal segment 170 to the proximal segment 160 of the vessel and then may enter a side lumen 180. Some of that embolic material may therefore be inadvertently delivered to another portion of the blood vessel tree (known as non-target embolization) and may cause unintended embolization in other healthy and vital parts of the body. That may cause serious complications. The need therefore exists for a novel methods and devices for injection of embolic agents that would make this procedure safer for the patient.

Another challenge during this procedure is that the regular infusion catheter does not allow the operator to perform a diagnostic angiogram during the infusion session concurrently with the infusion of the embolic material, to directly visualize the progression of the embolization. In order to infuse a radiopaque dye, the lumen of the catheter needs to be first cleared from the therapeutic agent and then the dye may be injected. Afterward, the opposite procedure needs to happen, which is to clear the lumen from the dye and fill it with another portion of the embolic material. This maneuver increases the operative time, and more importantly, increase the radiation dose to the patient and the operative staff.

A sole lumen available for injection causes difficulties in yet another situation, when during performing of embolization injection, the operator concomitantly needs to infuse a vasodilator agent or a pain medication into the embolization vascular vessel tree.

The need exists therefore for an infusion catheter allowing concurrent injection of various fluids and/or embolic particles into the target blood vessel area in a variety of clinical situations for facilitating better visualization of the vessel space surrounding the tip of the catheter while markedly reducing the risk of a non-target embolization.

SUMMARY

Accordingly, it is an object of the present invention to overcome these and other drawbacks of the prior art by providing a novel infusion catheter configured for injection of at least two different fluids at the same time while also equipped with an inflatable balloon to substantially slow down or stop the blood mixed with embolic agents in a blood vessel segment 170 reflux backward into vessel segment 160, thereby reducing or even completely eliminating any backflow of the embolic agent into the unintended blood vessel 180.

It is another object of the present invention to provide a method for injecting embolic agents while monitoring the location of the catheter tip in the vessel.

It is a further object of the present invention to provide an injection catheter with minimized risk of injecting embolic agent in a vessel other than a target vessel.

It is yet a further object of the present invention to provide an injection catheter with at least two injection lumens so that the embolic agent and the contrast agent or another liquid medication may be injected in any one of the lumens as appropriate for particular patient anatomy and other circumstances.

The injection catheter of the invention comprises an elongated tube featuring at least two lumens extending from a hub at a proximal end to a distal end thereof. The hub has two connectors in fluid communication with respective first and second lumens and is suitable for attaching an injection instrument thereto, such as a syringe. A first lumen is open at the distal end of the injection catheter to allow insertion thereof over a guidewire or injecting a desired fluid therethrough. A second lumen is terminated at a distal end of the injection catheter with a side opening leading to an interior of an inflatable balloon sealingly attached at the distal end at locations before and after the location of the side opening of the second lumen. The inflatable balloon is capable of inflating when fluid is injected through the second lumen to fill the interior of the inflatable balloon. The novel part is in the presence of one or more fenestrations or small openings in the balloon membrane making it possible for the fluid to proceed from the balloon interior to the outside space under controlled conditions. In use, inflation of the balloon with the desired fluid, for example, a contrast agent, causes expansion of the balloon followed by a slow leak of the contrast fluid from the distal portion of the balloon towards the target location, such as a location of the tumor. The inflated balloon is configured to create a pressure gradient between the proximal 160 and distal 170 segments of the blood vessel before and after the balloon. The intent of the inflated balloon is to temporary create low pressure environment in the distal blood vessel segment and therefore reduce the risk of backflow or diverting the contrast or embolic agents away from the target vessel 170.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail using the accompanying drawings, in which:

FIG. 2 is the same but with the balloon being inflated;

FIG. 3 is a close-up side view of the inflated balloon; and

FIG. 4 is a close-up front view of the same.

DETAILED DESCRIPTION OF PREFERRED EMBODIMENTS OF THE INVENTION

Figure 1:
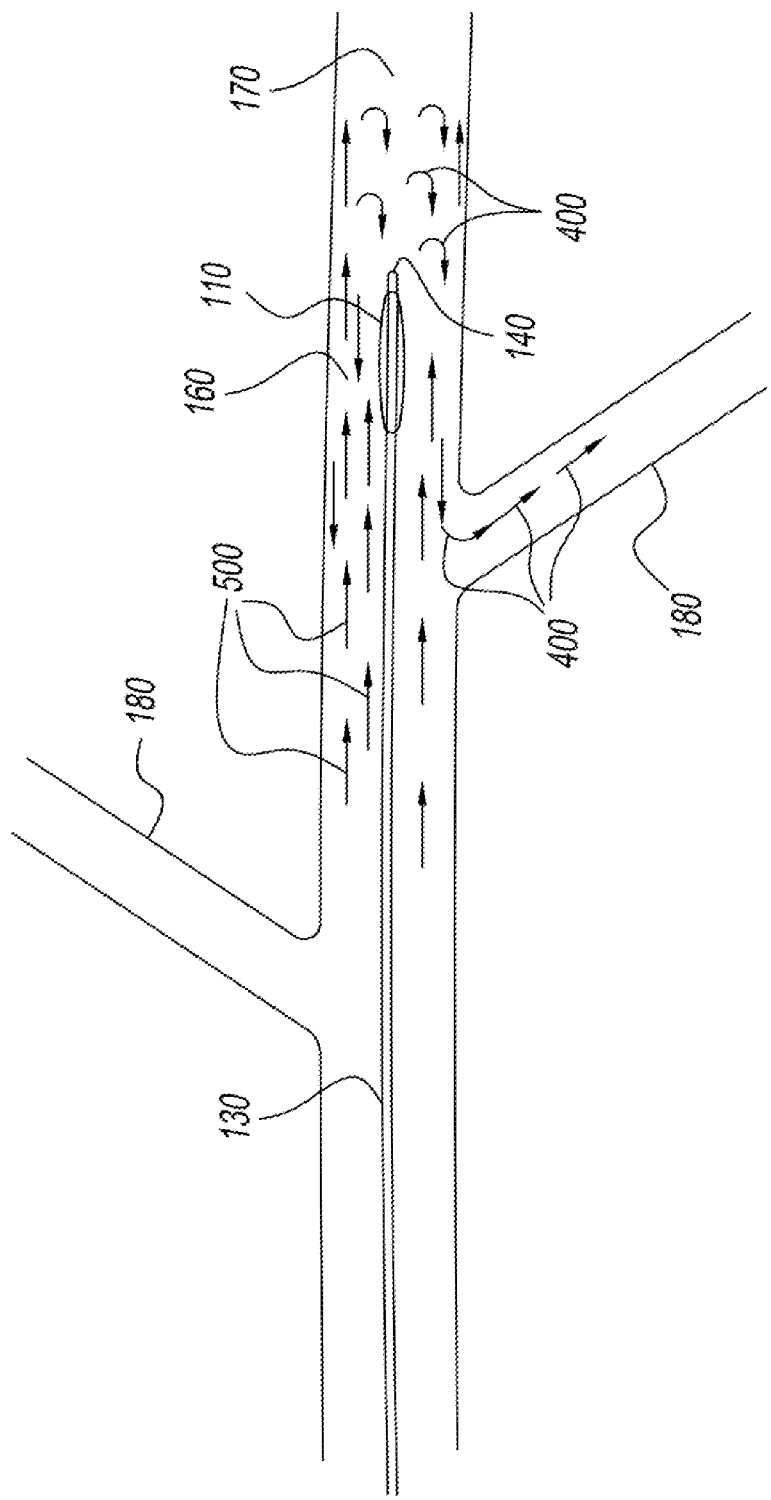
FIG. 1 is a side view of the injection catheter in a target vessel when the balloon is deflated.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The novel injection catheter of the present invention is aimed to address the following two objectives:

1. Allow infusion of the therapeutic agent (such as an embolic agent) without significant reflux and diversion to blood vessels other than the target vessel, and
2. Allow to simultaneously inject one fluid in one lumen (such as a contrast dye or medication) while injecting a second fluid (such as an embolic agent) into another lumen. This allows performing a diagnostic angiogram and, simultaneously, injecting the embolic agent so as to follow the progression of the embolic agent infusion and propagation through the target vessel without the need of clearing the catheter lumen from the therapeutic agent in order to inject the contrast agent or another liquid medication (vasodilator, painkiller) through the same lumen.

The injection catheter 130 has an elongated body of sufficient length to extend from an insertion site (such as a femoral artery or a radial artery) to a tumor location 170 or another target location inside the body. The diameter of the catheter 130 may be selected to facilitate minimally invasive or percutaneous insertion of the catheter over a guidewire, as known in the art. The catheter 130 may be made from a biocompatible material, such as polyurethane, and have sufficient stiffness to facilitate its advancement through a tortuous vessel path toward the target location.

At least two lumens are provided as part of the catheter 130: a first lumen is extending from the distal end to the proximal end and may be sized for use with a guidewire. The second lumen may also extend from the proximal end to the distal end but is terminated near the distal end with a side opening leading to an interior of an inflatable balloon 110 attached to the catheter 130 at the distal end thereof on both sides of the side opening. Each lumen may be equipped with an appropriate connector such as a Luer connector at the proximal end of the catheter to facilitate the injection of fluids into the lumens.

The inflatable balloon 110 may be made from a non-elastic or elastic membrane material. An elastic balloon membrane may be preferred as it allows inflating the balloon to the desired diameter based on specific dimensions of the vessel where it may be placed.

The first lumen 140 may be used to advance the catheter 130 over a guidewire (not shown) or, when the guidewire is removed, to inject a fluid therethrough. The second lumen may be used to inflate the balloon 110.

The novelty of the injection catheter of the present invention is the presence of at least one small opening 120 located on the membrane of the balloon 110, such as on the distal (anterior) portion thereof. Such opening may be sized to have a diameter or size of about 0.1 to about 2 mm, such as for example at least 0.1 mm, at least 0.2 mm, at least 0.4 mm, at least 0.6 mm, at least 0.8 mm, at least 1 mm, at least 1.2 mm, at least 1.4 mm, at least 1.6 mm, at least 1.8 mm, 2 mm or any diameter in between.

More than one opening 20 may be present on the anterior (most distal) portion of the membrane of the balloon 110, such as 2, 3, 4, 5, 6, 7, 8, 9, 10, 11, 12, 13, 14, 15, 16, 17, 18, 19, 20, or more openings.

At least some or all openings 120 may be located adjacent to each other. One, several, or all openings 120 may be made to have a circular shape, a slit-like shape (as seen in FIG. 4), another opening configured to serve as a one-way valve, or any other suitable shape.

To facilitate creating of the openings 120 and not cause tearing of the balloon 120, the balloon material may be reinforced or thickened in the area of the openings 120 prior to forming the openings by cutting, punching through, or laser cutting.

The presence of openings 120 makes the balloon 110 and the lumen leading to a new infusion pathway. This allows parallel injection of the contrast agent in one lumen and the embolic agent into the other lumen of the new injection catheter of the invention. This creates a lot of flexibility to use any of the lumens for injection of required fluids or for repositioning of the catheter over the guidewire. It also creates the ability to keep the guidewire in place during the embolization process in the event of catheter instability in certain circumstances (such as for blood vessels located in liver and lungs when the patient is unvoluntary coughing or rapidly breathing, making it challenging to keep the tip of the catheter in the intended vessel segment).

Ideally, the entire volume of the embolic agent has to reach the tumor location and avoid spilling or backflow into adjacent vessels so as not to damage healthy tissues surrounding the tumor. Having small openings 120 on the anterior portion of the balloon 110 allows close monitoring of the progress of embolic agent propagation along the target vessel.

Inflating the balloon 110 to the desired size also allows for better control of the propagation of the embolic agent downstream from the catheter tip in the area 170 of the blood vessel. Inflated balloon causes a temporary reduction or even a temporary complete arrest of blood flow 200 (FIG. 2) in the portion of the blood vessel surrounding the inflated balloon. Full or partial inflation of the balloon 110 creates a temporary pressure gradient between the normal blood pressure in the vessel segment 160 proximal to the balloon and the reduced blood pressure in the vessel segment 170 distal of the balloon 110. Pressure gradient across the balloon 110 may be used to slow down or speed up the propagation of the embolic agent 300 downstream of the balloon 110 as desired by the operator. It also makes it more difficult to any mixture of embolic agent and blood distal of the balloon 110 to backflow across a narrow space surrounding the balloon 110 and enter the unintended blood vessel 180.

Once the balloon 110 is inflated, the intravascular pressure (pressure in the blood vessel) imposed on the membrane wall of the inflated balloon 110 will deliver the embolic agent via the created opening(s) 120 on the anterior part of the balloon 110. The duration and extend of balloon inflation is directly proportional to the pressure applied to the plunger of the syringe at the operator's hand. The duration of balloon inflation determines the volume of the embolic agents delivered to the tumor. To access the degree of balloon inflation under fluoroscopy (X-RAY), the fluid injected in the balloon 110 may be mixed with sufficient amount of contrast dye. The embolic agent injection process may be cyclic (by periodic inflation from the syringe and deflation of the balloon from surrounding blood pressure), or continuous (during balloon inflation) as long as the operator keep sufficient pressure on the plunger of the syringe.

Once inflated, the balloon 110 cannot stay inflated without addition inflow of the fluid therein from the syringe, as the pressure of blood flow and the elasticity of the balloon wall would urge the fluid filling the balloon to escape through the plurality of openings 120 into the blood vessel portion distal to the balloon 110. This dynamic process assures that blood flow is inherently not interrupted for a long time. At the same time, this design allows the operator to select either the first lumen or the second lumen for infusion of the therapeutic agent or a contrast agent depending on their density and particle size.

At any specific time, while the therapeutic agent is being delivered, there will be some degree of balloon inflation and the subsequent pressure gradient between the two vessel segments 160, 170 before and after the balloon 110. This induced localized pressure gradient will minimize the degree of any backflow 400 markedly. This sequence of events will force the therapeutic agent to flow to the lower pressure area 170 of least resistance, which is advantageously located distal to the balloon 110 and, subsequently, to the target tumor location. The partially- or fully inflated balloon 110 can be used to create a temporary high-pressure gradient across the vessel segment before and after the balloon, thereby making it harder for the therapeutic agent delivered in the distal segment of the blood vessel to reverse direction and escape to another blood vessel, such as backflow 400 seen in FIG. 1.

Another advantage of the present injection catheter is that the first lumen may be used to inject other medications such as a vasodilator or an intraarterial lidocaine (if the patient develops pain or vasospasm during injection of the embolic agent), while the embolic agent is infused through the second balloon lumen. In addition, the guidewire can be kept in place within the catheter during therapeutic agent infusion—so as to add stability to the catheter tip in situations of unfavorable anatomy (short artery/landing zone of the catheter tip or breathing movement/tachypneic patient as in hepatic and bronchial vessels).

Importantly, all these maneuvers can be done without clearing of the first catheter lumen from the therapeutic agent. In case of an unexplained diversion of the embolic agent to another vessel or a catheter tip dislodge, there is no need to interrupt the procedure (or remove the catheter) or even to abort the procedure in case of radio-embolization.

In use, as the therapeutic agent gets infused thru the external port at the hub of the balloon lumen (such as via the attached syringe), the pressure in the balloon starts to build up. During this process, the balloon 110 is partially inflated and some of the therapeutic agent in the balloon is delivered out/forced out (intravascularly) thru the openings 120 located on the anterior surface of the balloon 110.

The extent of balloon inflation and the rate of therapeutic agent delivery depends on four factors:

1. The size and number of balloon openings 120, which is constant during a procedure;
2. The viscosity of the therapeutic agent, which may vary depending on how much contrast dye is added to the mixture. Usually, the contrast dye is added to the injected therapeutic agent to help visualize and monitor its progression. The current invention eliminates the need to add contrast dye to the therapeutic agent since local diagnostic angiogram/flow surveillance can be done frequently via the first catheter lumen. Therefore, no change in viscosity is expected for the specific therapeutic agent during the procedure;
3. Intra-syringe pressure as it relates to how fast the syringe plunger is being advanced; and
4. The intravascular blood pressure in the vessel segment 160 surrounding the balloon 110.

According to the present invention, a method of concurrently injecting two or more fluids in a blood vessel of a patient is provided, the method comprising the following steps:

a. providing an injection catheter comprising:
   a dual-lumen elongated tube extending from a distal end thereof to a hub at a proximal end thereof, wherein a first lumen of the elongated tube is open at the distal end, a second lumen of the elongated tube comprises a side opening at the distal end thereof leading to an interior of an inflatable balloon sealingly attached to the distal end of the elongated tube, the inflatable balloon comprises a balloon membrane with at least one opening therein to allow fluid communication between the interior of the inflatable balloon and outside thereof,
b. percutaneously inserting the injection catheter over a guidewire placed in the first lumen to position the distal end near a target site in the blood vessel,
c. injecting a first fluid into a second lumen to at least partially inflate the balloon while allowing the first fluid to proceed from the interior of the balloon through the at least one opening to the blood flow outside the balloon, and
d. concurrently injecting a second fluid into the first lumen as needed or repositioning the injection catheter over the guidewire positioned in the first lumen of the injection catheter,
   wherein either one of the first fluid or the second fluid are injected without a step of clearing the respective lumen from another fluid previously injected therethrough.

The use of the injection catheter of the invention reduces the number of variables and increases the reliability of targeted delivery of the embolic agent via achieving a controlled infusion delivery of the therapeutic agent with no significant backflow and no nontargeted embolization. Embolic agent delivery would only depend on two operator-dependent factors:

1. The rate of the therapeutic agent delivery, and
2. The degree of balloon inflation.

The injection catheter of the present invention has a number of important advantages over the prior art catheters:

1. Infusion the therapeutic agent into a more welcoming surrounding by increasing the pressure gradient across the balloon and making it harder for the therapeutic agent to backflow into a non-target blood vessel;
2. Ability to perform frequent diagnostic angiogram via the catheter lumen to follow the progress of the procedure and to intervene, if need be, for example when encountering an unexplained backflow of the embolic agent. Vasodilator and intraarterial lidocaine medication can be given during the procedure without the need of clearing the catheter lumen from the therapeutic agent as is the case with other catheters of the prior art;
3. The role of the two lumens can be reversed when the infused embolic agents need to be of large caliber (700-1200 um) in certain clinical situations. Presence of large openings 120 may make it difficult for the operator to keep the balloon inflated. Therefore, it is more advantageous to infuse large size particles of certain embolic agents using the first lumen while the balloon lumen is reserved to injection of diluted contrast dye—so as to keep the balloon inflated and create the favorable pressure gradient, as well as for injection of medication if needed. This switch of lumens allows to keep the openings 120 on a small side since the balloon 110 may be primarily used for fluid injection only;
4. The guidewire can be kept in place to give the catheter more stability during infusion. These scenarios of catheter tip instability can be seen in a small landing zone for the catheter (short artery) or a rapid oscillating organ (tachypneic or rapidly breathing/coughing patient); and
5. Using the current novel invention reduces the risk of backflow during embolization, thereby helping to shorten procedure/operation time, reduce radiation exposure to the patient and staff, as well as reduces cost. This is especially advantageous in a scenario of embolization of a nearby artery (right gastric, accessory hepatic, falciform arteries) in case of liver chemo- and radio-embolization, which usually takes a long time.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, Aft AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, Aft BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of concurrently injecting two or more fluids in a blood vessel of a patient, the method comprising the following steps:
    a. providing an injection catheter comprising:
    a dual-lumen elongated tube extending from a distal end of the injection catheter to a hub at a proximal end of the injection catheter, wherein a first lumen of the elongated tube is open at the distal end of the elongated tube, a second lumen of the elongated tube comprises a side opening at the distal end of the elongated tube leading to an interior of an inflatable balloon sealingly attached to the distal end of the elongated tube, the inflatable balloon comprises a balloon membrane with at least one opening within the balloon membrane to allow fluid communication between the interior of the inflatable balloon and outside of the inflatable balloon,
    b. percutaneously inserting the injection catheter over a guidewire placed in the first lumen to position the distal end of the injection catheter near a target site in the blood vessel,
    c. injecting a first fluid of the two or more fluids into the second lumen to at least partially inflate the inflatable balloon while allowing the first fluid to proceed from the interior of the inflatable balloon through the at least one opening to a flow of blood outside the inflatable balloon, wherein an extent of inflation of the inflatable balloon is defined solely by a balance of the first fluid incoming into the inflatable balloon from the second lumen and the first fluid proceeding through the at least one opening to mix with the flow of blood past the injection catheter, and
    d. concurrently with the injecting of the first fluid, injecting a second fluid of the two or more fluids into the first lumen as needed to enter the blood vessel past the injection catheter, or repositioning the injection catheter over the guidewire positioned in the first lumen of the elongated tube,
wherein the first fluid is injected without a step of clearing the second lumen from another fluid previously injected through the second lumen,
thereby improving a progression and safety of the method.

2. The method of concurrently injecting two or more fluids as in claim 1, wherein one of the first fluid or the second fluid contains a contrast agent, and the other fluid of the first fluid or the second fluid contains an embolic agent.

3. The method of concurrently injecting two or more fluids as in claim 1, wherein at least a partial inflation of the inflatable balloon increases a pressure gradient across segments of the blood vessel, reduces surrounding blood flow passing over the inflatable balloon in the blood vessel, and reduces a risk of backflow of any of the two or more fluids.

* * * * *